(12) United States Patent
Tournilhac et al.

(10) Patent No.: US 6,740,316 B2
(45) Date of Patent: May 25, 2004

(54) ANHYDROUS PIGMENT PASTE AND ITS USE IN COSMETICS

(75) Inventors: Florence Tournilhac, Paris (FR); Rolf Klucker, Bourg la Reine (FR)

(73) Assignee: L'Oreal, Paris (FR)

( * ) Notice: Subject to any disclaimer, the term of this patent is extended or adjusted under 35 U.S.C. 154(b) by 46 days.

(21) Appl. No.: 10/149,959

(22) PCT Filed: Oct. 19, 2001

(86) PCT No.: PCT/FR01/03260

§ 371 (c)(1),
(2), (4) Date: Oct. 15, 2002

(87) PCT Pub. No.: WO02/32382

PCT Pub. Date: Apr. 25, 2002

(65) Prior Publication Data

US 2003/0053969 A1 Mar. 20, 2003

(30) Foreign Application Priority Data

Oct. 19, 2000 (FR) .............................................. 00 13399

(51) Int. Cl.⁷ ........................... A61K 7/021; A61K 7/00; C04B 14/00; C04B 63/00; C08K 5/00
(52) U.S. Cl. ........................ 424/63; 106/400; 106/401; 106/402; 106/415; 106/425; 106/436; 106/456; 106/493; 106/494; 106/499; 424/400; 424/401
(58) Field of Search ................................ 424/400, 401, 424/63; 106/400, 401, 402, 415, 425, 436, 456, 493, 494, 499

(56) References Cited

U.S. PATENT DOCUMENTS 3,406,238 A    10/1968   Freyermuth et al.
6,423,785 B1 *  7/2002   Esselborn et al. ....... 525/327.6

FOREIGN PATENT DOCUMENTS

FR          2 772 605         6/1999
WO       WO 99/38925 A1 *    8/1999

* cited by examiner

Primary Examiner—Thurman K. Page
Assistant Examiner—Marina Lamm

(57) ABSTRACT

The invention relates to an anhydrous pigmentary paste comprising:
  from 20 to 32% by volume of at least one solid pigment, with respect to the total volume of the pigmentary paste,
  a pigment dispersion medium containing at least one anhydrous solvent selected from the hydrocarbon oils and the silicone oils, and
  a dispersing agent containing at least one imide or succinimide group linked by a covalent bond to a polymer chain compatible with the dispersion medium.

25 Claims, No Drawings

ANHYDROUS PIGMENT PASTE AND ITS USE IN COSMETICS

The present invention relates to an anhydrous pigmentary paste for colouring cosmetic compositions, comprising solid pigments, dispersed in a continuous medium by a dispersing agent.

By pigmentary paste should be understood a concentrated colloidal dispersion of pigments in a continuous medium, or dispersion medium, stabilized by a dispersing agent, or without a dispersing agent.

A concentrated colloidal dispersion should be understood to mean a suspension of particles of micron size, in other words less than 10 μm, in a continuous medium. The volume fraction of particles in a concentrated dispersion is of the order of 20 to 40%, preferably greater than 30%. Any liquid required for the dispersion may take the place of the continuous medium, for example water, glycol, solvents, fats and their mixtures.

The dispersing agent protects the dispersed particles against agglomeration or flocculation. The dispersing agent may be a surface-active agent, an oligomer, a polymer or a mixture of a number of these, bearing one or more functional groups with a strong affinity for the surface of the particle to be dispersed.

These pigments are difficult to disperse in hydrocarbon oils or silicone oils, conventionally used in lipsticks, and tend to agglomerate, even in the presence of conventional dispersing agents. This limits the maximum concentration of pigments in the oil, and impairs the fluidity of such a dispersion.

The use of dispersing agents in pigmentary pastes is known in the prior art. However, the pigmentary pastes containing these organic pigments in the presence of a conventional dispersing agent are relatively thick and have high viscosity, causing the dispersing agent to have a poor adsorption affinity for the surface of the organic pigments.

The object of the invention is thus a pigmentary paste which overcomes the disadvantages of the prior art.

The object of the invention is in particular an anhydrous pigmentary paste containing a dispersing agent with a good adsorption affinity for the surface of the pigments, particularly that of organic pigments. The presence of such an agent has the advantage of creating the possibility of producing pigmentary pastes with low viscosity, while maintaining a high concentration of pigments.

A further object of the invention is the use of an anhydrous pigmentary paste according to the invention to colour cosmetic compositions, and in particular lipsticks.

A further object of the invention is a cosmetic composition containing a cosmetically acceptable medium and a pigmentary paste according to the invention.

In the context of this application, cosmetically acceptable means a composition with a pleasant appearance, odour, taste and feel.

The objectives of the present invention are achieved by producing an anhydrous pigmentary paste comprising:
- from 20 to 32% by volume of at least one solid pigment, with respect to the total volume of pigmentary paste,
- a pigment dispersion medium containing at least one anhydrous solvent selected from the hydrocarbon oils and the silicone oils, and
- a dispersing agent which is a polymer containing at least one imide or succinimide group linked by a covalent bond to a polymer chain compatible with the dispersion medium.

The imide or succinimide group or groups may be side or end groups, preferably end groups.

Compatible polymer chain means a polymer or oligomer chain soluble in the continuous phase of the dispersion.

The polymer advantageously has a molecular weight of at least 600 g, and preferably from 1000 to 1500 g.

The preferred polymer chains according to the invention are the polyolefins, such as the polyethylenes, the polypropylenes and the polyisobutylenes and other poly α-olefins. The particularly preferred polymer chains are the polyisobutylenes.

The dispersing agents which may be used according to the invention are preferably polymers obtained by condensation of an amine with a succinic anhydride having a saturated or unsaturated hydrocarbon chain, whose synthesis is disclosed in the U.S. Pat. No. 3,172,892. The preferred dispersing agents are polyisobutylenes containing at least one succinimide group, preferably a terminal succinimide group. These dispersing agents advantageously have a polymer chain of molecular weight of at least 600 g, and preferably from 1000 to 1500 g. Such dispersing agents are disclosed in the U.S. Pat. No. 3,172,892 and U.S. Pat. No. 3,235,484, and are known under the name of LUBRIZOL™. A particularly preferred dispersing agent is the polyisobutylene succinimide marketed under the trade name LUBRIZOL™ 0517134.

The dispersing agent generally represents from 1 to 10% of the total weight of the pigmentary paste, and preferably of the order of 5%.

The pigmentary paste according to the invention also contains a pigment normally used in cosmetic or dermatological compositions.

The pigments which may be used according to the invention may be inorganic or organic, white or coloured, or nacres, or their mixtures.

The inorganic pigments include titanium dioxide, optionally surface-treated, or zinc dioxide, zirconium or cerium oxides, and the iron and chromium oxides, manganese violet, ultramarine blue, chromium hydrate and ferric blue, and their mixtures. The preferred inorganic pigments are the iron oxides, especially red iron oxide, yellow iron oxide, red and yellow iron oxide, brown iron oxide, black iron oxide, titanium dioxide and their mixtures.

The organic pigments include:
- the pure organic pigments, such as carbon black or those which may or may not have a FDA certification, such as D&C Red No 36, and
- the pigments of the organic lake type, such as the organic lakes of barium, strontium, calcium or aluminium with a FDA certification or exempt from FDA certification such as the lakes based on cochineal carmine, D&C Red No 7 calcium lake, D&C Red No 27 aluminium lake, D&C Red No 21 aluminium lake, FD&C Yellow No 5 aluminium lake, FD&C Yellow No 6 aluminium lake, D&C Red No 7 and FD&C Blue No 1 aluminium lake, and their mixtures.

The nacre pigments may be selected from the white nacre pigments, such as mica coated with titanium or bismuth oxychloride, the coloured nacre pigments such as titanium mica with iron oxides, titanium mica with in particular ferric blue or chromium oxide, titanium mica with an organic pigment of the type mentioned above.

The dispersing agent according to the invention has a good affinity for the surface of the pigments, and especially the organic pigments.

The dispersion medium of the solid pigments contains at least one anhydrous solvent selected from the hydrocarbon oils and the silicone oils. These oils may be polar or non-polar oils, volatile or non-volatile, usable in cosmetics.

The polar oils include the hydrocarbon oils containing ester, ether, acid or alcohol functions or their mixtures, such as for example:

the plant hydrocarbon oils with a high content of triglycerides consisting of esters of fatty acids and glycerol, of which the fatty acids may have varying chain lengths and may be linear or branched and saturated or unsaturated; these oils particularly include wheat germ, corn, sunflower, shea, sweet almond, macadamia, apricot, soya, rapeseed, cotton, alfalfa, poppy, pumpkin, sesame, marrow, avocado, hazelnut, grapeseed, blackcurrant, evening primrose, millet, barley, quinoa, olive, rye, safflower, bancoulier, passion flower, rose hip oils, or castor oil; or triglycerides of caprylic/capric acids such as those marketed by the Company Stearineries Dubois or those marketed under the trade names Miglyol™ 810, 812 and 818 by the Company Dynamit Nobel, the synthetic oils of formula $R^1COOR^2$ in which $R^1$ represents a linear or branched higher fatty acid residue, containing from 7 to 19 carbon atoms, and $R^2$ represents a branched hydrocarbon chain containing from 3 to 20 carbon atoms, such as for example Purcellin oil (ketostearyl octanoate), isononyl isononanoate, the $C_{12}$ to $C_{15}$ alcohol benzoates.

the synthetic esters and ethers such as isopropyl myristate, 2-ethylhexyl palmitate, the octanoates, decanoates or ricinoleates of alcohols or polyalcohols, the hydroxyl esters such as isostearyl lactate, diisostearyl malate, and the pentaerythritol esters;

the $C_8$ to $C_{26}$ fatty alcohols such as oleic alcohol; and their mixtures.

The anhydrous solvent is preferably an apolar oil.

The apolar oils include:

the silicone oils which may be volatile or non-volatile, linear or cyclic, liquid at ambient temperature, such as the polydimethylsiloxanes (PDMS) containing alkyl, alkoxy or phenyl groups, pendant or at the end of the silicone chain and having from 2 to 24 carbon atoms; the phenylated silicones, such as the phenyl trimethicones, the phenyl dimethicones, the phenyl trimethylsiloxy diphenylsiloxanes, the diphenyidimethicones, the diphenyl methyldiphenyl trisiloxanes, the 2-phenylethyl trimethylsiloxysilicates, and their mixtures.

the hydrocarbons or fluorinated hydrocarbons, which may be linear or branched and of synthetic or inorganic origin, such as the paraffin oils (for example the isoparaffins), and the aliphatic hydrocarbons which may be volatile (for example isododecane), or non-volatile and their derivatives, vaseline, the polydecenes, hydrogenated polyisobutene such as Parleam™, squalane, and their mixtures.

The anhydrous solvent is preferably an apolar hydrocarbon oil, of synthetic or inorganic origin, selected in particular from the hydrocarbons, especially alkanes, such as Parleam™ (hydrogenated polyisobutene), isoparaffins including isododecane, squalane, and their mixtures. The particularly preferred anhydrous solvent is Parleam™ (hydrogenated polyisobutene).

The pigmentary pastes according to the invention generally have a viscosity of from 2 to 25 Poises (0.2 to 2.5 Pa·s), preferably 10 Poises (1 Pa·s) or less, and more preferably 5 Poises (0.5 Pa·s) or less, the viscosity being evaluated at ambient temperature (20 to 25° C.), with a shearing rate of 200 s$^{-1}$, using a Rhéomat RM 180 viscometer with mobiles 2 or 3 depending on their suitability for the viscosity of the pigmentary paste.

The pigmentary pastes according to the invention are particularly suitable for colouring cosmetic compositions, and especially in the formulation of lipsticks.

The following examples illustrate the invention without in any way limiting its scope.

In the examples, except where otherwise stated, all quantities are expressed as weight fractions with respect to the total weight of the pigmentary paste.

EXAMPLES

The pigmentary pastes PP1 to PP5 according to the invention were prepared by mixing the ingredients listed in table 1 below as follows:

1. the dispersing agent was dissolved in Parleam™, at a temperature of about 80° C., over 10 to 15 minutes, so as to ensure complete dissolution of the dispersing agent;
2. the pigments were then progressively added to Parleam™ with stirring by a deflocculant disk, to ensure complete mixing of the pigments, then the mixture was homogenized for about 15 minutes;
3. this mixture was then milled in a DISPERMAT grinder for 35 to 40 minutes, at a temperature of 25 to 30° C.

For each pigmentary paste PP1 to PP5, the viscosity was measured at ambient temperature (20 to 25° C.) with a shearing rate of 200 s$^{-1}$, with a Rhéomat RM 180 viscometer with mobiles 2 or 3 depending on their suitability for the viscosity of the pigmentary paste.

The results of the viscosity measurements for the pigmentary pastes PP1 to PP5 are given in table 2.

TABLE I

| composition (%) | PP1 | PP2 | PP3 | PP4 | PP5 |
|---|---|---|---|---|---|
| D & C Red No 36 | 40% | 40% (26.1% by volume) | — | — | — |
| D & C Red No 7 | — | — | 30% | 30% | 40% |
| Parleam ™ | 57% | 55% | 67% | 65% | 55% |
| LUBRIZOL OS17134AZ | 3% | 5% | 3% | 5% | 5% |

TABLE 2

| | PP1 | PP2 | PP3 | PP4 | PP5 |
|---|---|---|---|---|---|
| viscosity [Poise] | 6 | 4.8 | 6.7 | 2.7 | 13.2 |

Table 2 shows that the pigmentary pastes according to the invention PP1 to PP5 have low viscosity, in other words lower than 15 Poises, for a high weight fraction of pigment.

Table 2 also shows that, for the same quantity of pigment, an increase in the weight fraction of dispersing agent leads to a further decrease in the viscosity.

What is claimed is:

1. A paste comprising from 20 to 32% by volume of at least one solid pigment, with respect to the total volume of paste, a pigment dispersion medium comprising at least one anhydrous solvent selected from the group consisting of hydrocarbon oils and silicone oils, and a dispersing agent which is a polymer comprising at least one imide or succinimide group linked by a covalent bond to a polymer chain compatible with the dispersion medium.

2. The paste according to claim 1, wherein the polymer chain has a molecular weight of at least 600 g.

3. The paste according to claim 1, wherein the polymer chain has a molecular weight of from 1000 to 1500 g.

4. The paste according to claim 1, wherein the polymer chain is a polyolefin.

5. The paste according to claim 1, wherein the polymer chain is a polyisobutylene.

6. The paste according to claim 1, wherein the dispersing agent is a polyisobutylene succinimide.

7. The paste according to claim 1, wherein the dispersing agent is a polymer obtained by condensing an amine with a succinic anhydride attached to a saturated or unsaturated hydrocarbon chain.

8. The paste according to claim 1, wherein the weight fraction of the dispersing agent in the paste is from 1 to 10% of the total weight of the paste.

9. The paste according to claim 1, wherein the pigment is selected from the group consisting of inorganic pigments, organic pigments, nacre pigments and mixtures thereof.

10. The paste according to claim 9, comprising one or more inorganic pigments, wherein the inorganic pigments are selected from the group consisting of titanium dioxide, zinc dioxide, red iron oxide, yellow iron oxide, brown iron oxide, black iron oxide, and mixtures thereof.

11. The paste according to claim 9, comprising one or more organic pigments wherein the organic pigments are selected from the group consisting of pure organic pigments and pigments of the lake type.

12. The paste according to claim 9, comprising the organic pigment D&C Red No36.

13. The paste according to claim 9, comprising one or more pigments of the lake type, wherein the pigment is a lake selected from the group consisting of organic lakes of barium, organic lakes of strontium, organic lakes of calcium, organic lakes of aluminium, lakes based on cochineal carmine, D&C Red No 7 calcium lake, D&C Red No 27 aluminium lake, D&C Red No 21 aluminium lake, FD&C Yellow No 5 aluminium lake, FD&C Yellow No 6 aluminium lake, D&C Red No 7, FD&C Blue No 1 aluminium lake and mixtures thereof.

14. The paste according to claim 9, comprising one or more nacre pigments selected from the group consisting of mica coated with titanium, mica coated with bismuth oxychloride, titanium mica with iron oxides, titanium mica with ferric blue, titanium mica with chromium oxide, and titanium mica with an organic pigment.

15. The paste according to claim 1, wherein the anhydrous solvent is an apolar oil.

16. The paste according to claim 1, wherein the anhydrous solvent is an apolar hydrocarbon oil selected from the group consisting of hydrogenated polyisobutene, squalane, aliphatic hydrocarbons and mixtures thereof.

17. The paste according to claim 1, wherein the anhydrous solvent is a silicone oil selected from the group consisting of polydimethylsiloxanes (PDMS) and phenylated silicones.

18. The paste according to claim 1, wherein the viscosity is from 2 to 25 Poises (0.2 to, 2.5 Pa·s) measured at ambient temperature (20–25° C.) with a shearing rate of 200 s$^{-1}$.

19. A cosmetic composition comprising a cosmetically acceptable medium and the paste of claim 1.

20. A method for coloring a composition, comprising:
mixing the paste of claim 1 with the composition.

21. The paste of claim 14, comprising titanium mica with an organic pigment selected from the group consisting of pigment D&C Red No. 36, organic lakes of barium, organic lakes of strontium, organic lakes of calcium, organic lakes of aluminium, lakes based on cochineal carmine, D&C Red No 7 calcium lake, D&C Red No 27 aluminium lake, D&C Red No 21 aluminium lake, FD&C Yellow No 5 aluminium lake, FD&C Yellow No 6 aluminium lake, D&C Red No 7, FD&C Blue No 1 aluminium lake and mixtures thereof.

22. The paste according to claim 1, wherein the weight fraction of the dispersing agent in the paste is of the order of 5%.

23. The paste of claim 17, comprising a phenylated silicone selected from the group consisting of phenyl trimethicones, phenyl dimethicones, diphenyl dimethicones, diphenyl methyldiphenyl trisiloxanes, 2-phenylethyl trimethylsiloxysilicates and mixtures thereof.

24. The paste according to claim 18, wherein the viscosity is 10 Poises (1Pa·s) or less.

25. The paste according to claim 18, wherein the viscosity is 5 Poises (0.5 Pa·s) or less.

* * * * *